(12) United States Patent
Zhang et al.

(10) Patent No.: US 12,114,885 B2
(45) Date of Patent: Oct. 15, 2024

(54) CUTTING DEVICE AND CUTTING BALLOON

(71) Applicant: BrosMed Medical Co., Ltd., Dongguan (CN)

(72) Inventors: Zhijun Zhang, Dongguan (CN); Junyi Huang, Dongguan (CN); Lingbo Wu, Dongguan (CN)

(73) Assignee: BROSMED MEDICAL CO., LTD., Guangdong (CN)

( * ) Notice: Subject to any disclaimer, the term of this patent is extended or adjusted under 35 U.S.C. 154(b) by 403 days.

(21) Appl. No.: 17/616,564

(22) PCT Filed: Apr. 30, 2020

(86) PCT No.: PCT/CN2020/088325
§ 371 (c)(1),
(2) Date: Dec. 3, 2021

(87) PCT Pub. No.: WO2021/217590
PCT Pub. Date: Nov. 4, 2021

(65) Prior Publication Data
US 2022/0192692 A1  Jun. 23, 2022

(51) Int. Cl.
*A61B 17/3207* (2006.01)
*A61B 17/22* (2006.01)

(52) U.S. Cl.
CPC .......... *A61B 17/3207* (2013.01); *A61B 17/22* (2013.01); *A61B 2017/22061* (2013.01)

(58) Field of Classification Search
CPC ................ A61B 17/3207; A61B 17/22; A61B 2017/22061; A61B 17/320725; A61B 17/3209; A61M 2025/109
See application file for complete search history.

(56) References Cited

U.S. PATENT DOCUMENTS

2004/0092956 A1* 5/2004 Liddicoat .............. A61M 27/00
606/1
2004/0127920 A1 7/2004 Radisch, Jr.
(Continued)

FOREIGN PATENT DOCUMENTS

CN 1568165 A 1/2005
CN 105708511 A 6/2016
(Continued)

OTHER PUBLICATIONS

International Search Report and Written Opinion of PCT/CN2020/088325 mailed Jan. 28, 2021.

*Primary Examiner* — Sarah A Long
*Assistant Examiner* — James R McGinnity
(74) *Attorney, Agent, or Firm* — Peter J. Ims; Westman, Champlin & Koehler, P.A.

(57) ABSTRACT

The present application disclosed a cutting device and a cutting balloon, the cutting device includes a connection tube, at least one cutting component and a collapsible tube; the collapsible tube is made of elastic material and configured to be sleeved on the connection tube; the at least one cutting component includes a cutter body and cutting connection segments connected to the cutter body, the cutting connection segments are connected to a peripheral side of the connection tube (100) and are located in the collapsible tube; and the collapsible tube is in elastic contact against the cutting connection segments.

18 Claims, 4 Drawing Sheets

(56) References Cited

U.S. PATENT DOCUMENTS

| | | | |
|---|---|---|---|
| 2005/0021071 A1* | 1/2005 | Konstantino | A61M 25/104 606/194 |
| 2006/0182873 A1 | 8/2006 | Klisch et al. | |
| 2014/0277002 A1 | 9/2014 | Grace | |
| 2015/0133978 A1* | 5/2015 | Paul, Jr. | A61B 17/320725 606/159 |
| 2016/0249942 A1* | 9/2016 | Olson | A61M 25/104 604/509 |
| 2017/0100570 A1 | 4/2017 | Giasolli et al. | |
| 2018/0028221 A1 | 2/2018 | Silvestro | |
| 2018/0185051 A1 | 7/2018 | Boyle et al. | |
| 2019/0307992 A1 | 10/2019 | Haverkost et al. | |
| 2020/0078045 A1* | 3/2020 | Wallace | A61B 17/320758 |
| 2021/0113235 A1* | 4/2021 | Chanduszko | A61M 25/104 |

FOREIGN PATENT DOCUMENTS

| | | |
|---|---|---|
| CN | 206304214 U | 7/2017 |
| CN | 107496009 A | 12/2017 |
| CN | 109893215 A | 6/2019 |
| CN | 110198677 A | 9/2019 |
| CN | 110478602 A | 11/2019 |
| CN | 110840527 A | 2/2020 |
| CN | 210020798 U | 2/2020 |
| CN | 108577937 A | 9/2020 |
| JP | 2011245114 A | 12/2011 |
| JP | 2013176507 A | 9/2013 |
| WO | 9007909 A1 | 7/1990 |
| WO | 2020032918 A1 | 2/2020 |

* cited by examiner

CUTTING DEVICE AND CUTTING BALLOON

CROSS-REFERENCE TO RELATED APPLICATION

This application is a Section 371 National Stage Application of International Application No. PCT/CN2020/088325, filed Apr. 30, 2020, the content of which is incorporated herein by reference.

FIELD

The present application relates to the technical field of medical apparatus and instruments, and more particularly to a cutting device and a cutting balloon.

BACKGROUND

A cutting balloon can be used to treat vascular stenosis, which generally includes a catheter, a balloon body connected to the catheter, and a cutting device covering a peripheral side of the balloon body and connected to the catheter. When the balloon body is expanded at the lesion, the cutting device can incise the calcified plaque and the blood vessel wall along the longitudinal direction of the blood vessel, which can greatly reduce the annular pressure generated on the blood vessel wall when the balloon body is expanded and reduce blood vessel damage.

The cutting device generally includes a plurality of cutting components and connection tubes for connecting each cutting component and the catheter. However, in the related industries, each cutting component is usually directly adhered to the peripheral side of the connection tube, resulting in a greater risk of the cutting component falling off from the connection tube.

SUMMARY

An object of embodiments of the present application is to provide a cutting device and a cutting balloon, in order to solve the problem that each cutting component is in a greater risk of falling off.

In order to solve the above technical problem, the technical scheme adopted by embodiment of the present application is:

In first aspect, a cutting device is provided, which including:
a connection tube;
a collapsible tube, made of elastic material and configured to be sleeved on the connection tube; and
at least one cutting component, comprising a cutter body and cutting connection segments connected to the cutter body, the cutting connection segments are connected to a peripheral side of the connection tube and are located on the collapsible tube;
the collapsible tube is in elastic contact against the cutting connection segments.

In an embodiment, the cutting connection segments are of a flat shape.

In an embodiment, the cutting component further comprises a transition connection segment configured to connect between the cutter body and the cutting connection segment, and a cross-sectional dimension of the transition connection segment is gradually tapered from a side thereof connected to the cutter body to another side.

In an embodiment, the cutting connection segments are formed by an extrusion process or a cutting process.

In an embodiment, a side surface of the cutting connection segment facing the collapsible tube is provided with at least one non-slip ridge.

In an embodiment, the collapsible tube is a collapsible tube made of a rubber.

In an embodiment, a length of the connection tube is larger than 0.5 mm.

In an embodiment, the length of the connection tube is 1 mm.

In an embodiment, a ratio of a length of the cutting connection segment to a length of the connection tube is larger than or equal to 0.8.

In an embodiment, the length of the cutting connection segment is equal to the length of the connection tube.

In an embodiment, the cutter body has a triangular, circular or trapezoidal cross-sectional shape.

In an embodiment, a number of the connection tube and the collapsible tube are two, and the two connection tubes are respectively connected to two ends of the cutting component, and the two collapsible tubes are elastically sleeved on the two connection tubes respectively.

In an embodiment, a number of the cutting component is 3 to 5.

In an embodiment, each the cutting component is arranged in array relative to a periphery of the connection tube.

In an embodiment, the connection tube is a connection tube made of a metal or alloy that does not transmit X-rays.

In an embodiment, the cutting component is a cutting component made of a metal or alloy.

In an embodiment, the cutting component is adhered or welded to a peripheral side of the connection tube.

In an embodiment, a calculation formula of a length of the cutting component is:

$$y = kx^b.$$

wherein y represents a length of the cutting component; x represents a length of the connection tube; a value range of k is 55~65; and a value range of b is 1.6~1.8.

In an embodiment, the value of k is 60, and/or the value of b is 1.7.

In second aspect, a cutting balloon is provided, which including:
a catheter; and
a balloon body, connected to the catheter;
the cutting balloon further includes the cutting device, and the cutting device is connected with the catheter through the collapsible tube.

The beneficial effect of the cutting device provided by the embodiment of the present application is that: firstly, the cutting connection segments of the cutting component are connected to the peripheral side of the connection tube, and then the collapsible tube made of elastic material is sleeved on the connection tube and the peripheral side of the cutting component, such that an elastic resisting force onto the cutting component is formed based on an elastic performance of the collapsible tube, therefore the cutting component can be firmly fixed between the collapsible tube and the connection tube, effectively reducing the risk of the cutting component falling off, especially, the risk of falling off of the cutting component during the operation is reduced, and the performance of the cutting device is largely guaranteed.

BRIEF DESCRIPTION OF DRAWINGS

In order to explain the embodiments of the present application more clearly, a brief introduction regarding the accompanying drawings that need to be used for describing the embodiments of the present application or the prior art is given below; it is obvious that the accompanying drawings described as follows are only some embodiments of the present application, for those skilled in the art, other drawings can also be obtained according to the current drawings on the premise of paying no creative labor.

Figure 1:
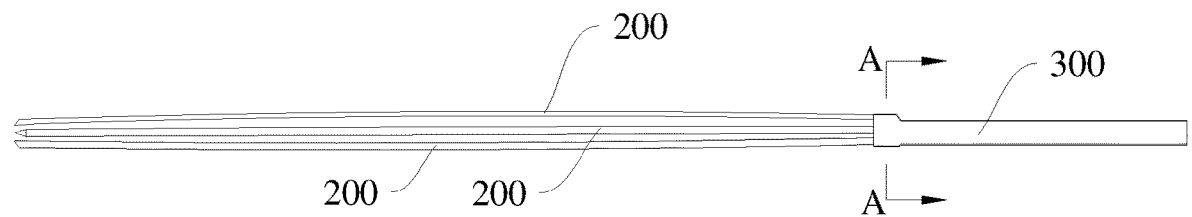
FIG. 1 is a structural schematic view of a cutting device provided by an embodiment of the present application.

In the drawings, like element are numbered alike; 100—connection tube; 200—cutting component; 210—cutter body; 220—cutting connection segment; 221—non-slip ridge; 230—transition connection segment; 300—collapsible tube; 100'—catheter; 200'—balloon body.

DETAILED DESCRIPTION

In order to make the purpose, the technical solution and the advantages of the present application be clearer and more understandable, the present application will be further described in detail below with reference to accompanying figures and embodiments. It should be understood that the specific embodiments described herein are merely intended to illustrate but not to limit the present application.

In the description of the present application, it needs to be understood that, directions or location relationships indicated by terms such as "length", "width", "up", "down", "front", "rear", "left", "right", "vertical", "horizontal", "top", "bottom", "inside", "outside", and so on are the directions or location relationships shown in the accompanying figures, which are only intended to describe the present application conveniently and simplify the description, but not to indicate or imply that an indicated device or component must have specific locations or be constructed and manipulated according to specific locations; therefore, these terms shouldn't be considered as any limitation to the present application.

In addition, terms "the first" and "the second" are only used in describe purposes, and should not be considered as indicating or implying any relative importance, or impliedly indicating the number of indicated technical features. As such, technical feature(s) restricted by "the first" or "the second" can explicitly or impliedly comprise one or more such technical feature(s). In the description of the present application, "a plurality of" means two or more, unless there is additional explicit and specific limitation.

In the present application, unless there is additional explicit stipulation and limitation, terms such as "mount", "connect with each other", "connect", "fix", and so on should be generalizedly interpreted, for example, "connect" can be interpreted as being fixedly connected, detachably connected, or connected integrally; "connect" can also be interpreted as being mechanically connected or electrically connected; "connect" can be further interpreted as being directly connected or indirectly connected through intermediary, or being internal communication between two components or an interaction relationship between the two components. For the one of ordinary skill in the art, the specific meanings of the aforementioned terms in the present application can be interpreted according to specific conditions.

Figure 2:
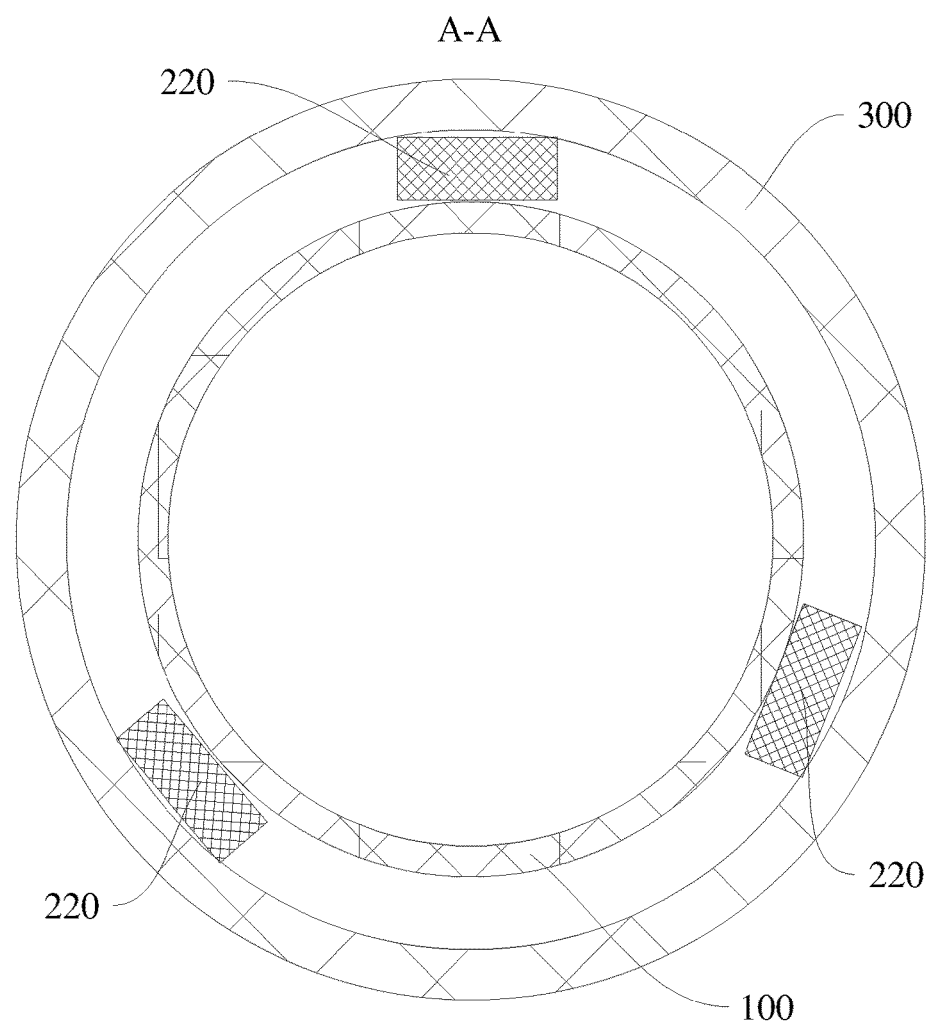
FIG. 2 is a cross-sectional schematic view of A-A section of a cutting device provided by FIG. 1.
Figure 3:
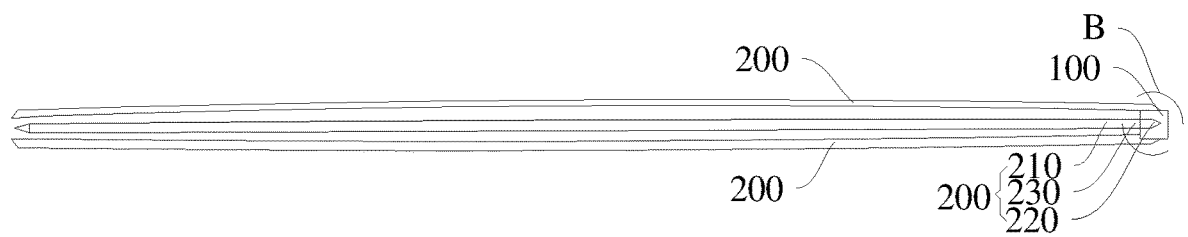
FIG. 3 is a structural schematic view 1 of a cutting component and connection tube provided by an embodiment of the present application.

The following describes the specific implementation of the present application in more detail with reference to specific embodiments:

Please refer to FIG. 1, FIG. 2 and FIG. 3, an embodiment of the present application provides a cutting device, and the cutting device includes a connection tube 100, cutting components 200 and a collapsible tube 300. The collapsible tube 300 is made of an elastic material and is sleeved on the connection tube 100; the cutting component 200 is provided with at least one, and each the cutting component 200 includes a cutter body 210 and cutting connection segments 220 connected to the cutter body 210, and the cutting connection segments 220 are connected to the peripheral side of the connection tube 100 and are located in the collapsible tube 300; the collapsible tube 300 is in elastic contact against the cutting connection segments 220.

It should be noted here that the cutting connection segments 220 are connected to the end side of the cutter body 210. The cutting connection segments 220 may be provided at one end of the cutter body 210, or the cutting connection segments 220 may be provided at both ends of the cutter body 210. The cutting connection segments 220 are connected to the outer surface of the connection tube 100 to initially fix the cutting component 200. Optionally, the cutting component 200 can be a micro blade or a cutting wire.

The collapsible tube 300 is made of an elastic material and has certain elastic properties. On the basis of connecting the cutting connection segment 220 to the peripheral side of the connection tube 100, the collapsible tube 300 is sleeved on the peripheral side of the cutting connection segments 220 and the connection tube 100, such that the collapsible tube 300 produce a balanced and expanded elastic deformation along each radial direction, thus, a balanced elastic resisting force facing the side of the connection tube 100 and along each radial direction can be generated on the cutting connection segments 220 in contact with the inner surface thereof, so that the cutting connection segments 220 can be closely in contact with the peripheral side of the connection tube 100. Based on the connection relationship between connection tube 100 and cutting connection segments 220, combined with the elastic resistance of the collapsible tube 300, the connection strength of the cutting component 200, the connection tube 100 and the collapsible tube 300 can be effectively enhanced, thereby effectively reducing the risk of the falling off of the cutting component 200.

In summary, by adopting the above scheme, the cutting connection segments 220 of the cutting component 200 can be connected to the peripheral side of the connection tube 100 firstly, and then the collapsible tube 300 made of elastic material is sleeved on the connection tube 100 and the peripheral side of the cutting component 200, such that an elastic resisting force onto the cutting component 200 is formed based on an elastic performance of the collapsible tube 300, therefore the cutting component 200 can be firmly fixed between the collapsible tube 300 and the connection tube 100, effectively reducing the risk of the cutting component 200 falling off, especially, the risk of falling off of the cutting component during the operation is reduced, and the performance of the cutting device is largely guaranteed.

Figure 4:
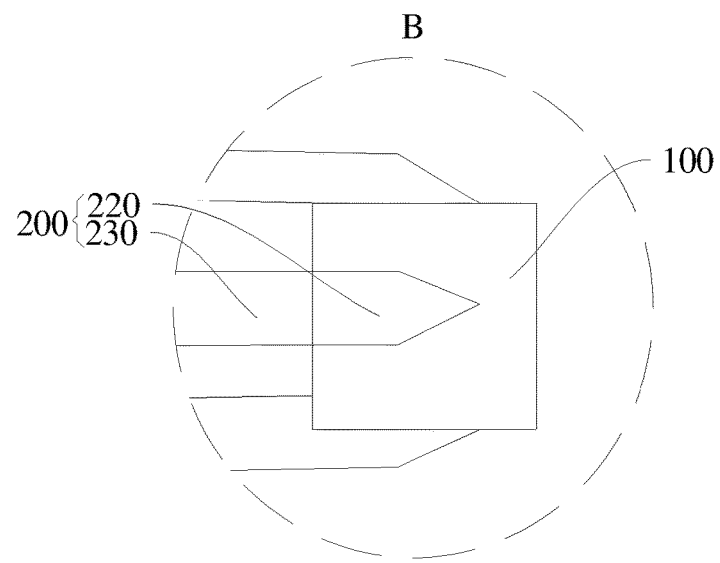
FIG. 4 is an enlarged view of area B of a cutting component and connection tube provided FIG. 3.
Figure 5:
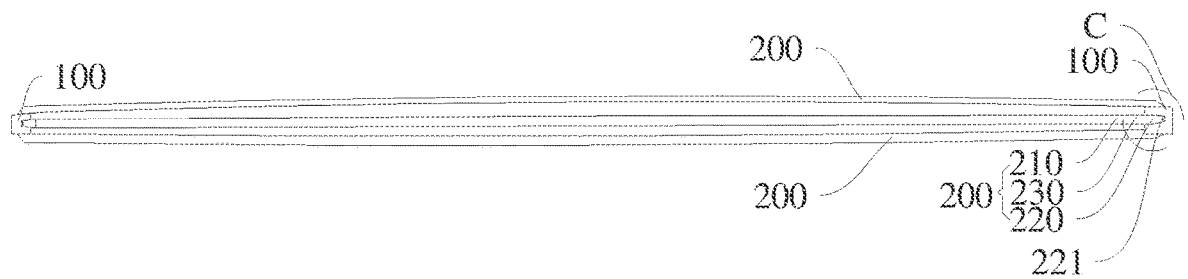
FIG. 5 is a structural schematic view 2 of a cutting component and connection tube provided by an embodiment of the present application.
Figure 6:
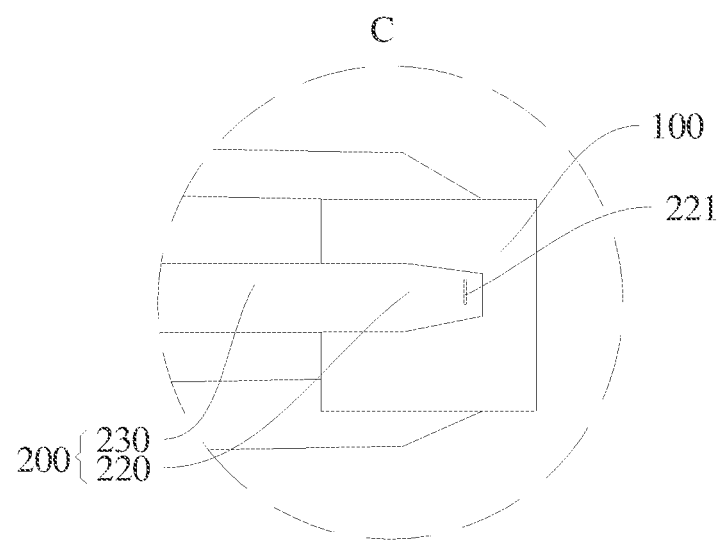
FIG. 6 is an enlarged view of area C of a cutting component and connection tube provided FIG. 5.

Optionally, as shown in FIGS. 3-4 and 5-6, on the basis of guaranteeing the connection strength of the connection tube 100 and the cutting connection segments 220. The present embodiment does not limit the shape of the cutting connection segment 220 in any way. Among them, as shown in FIGS. 5-6, the contact area of the cutting connection segments 220 and the connection tube 100 is larger, and the connection strength is stronger. Therefore, the cutting connection segment 220 shown in FIGS. 5-6 may be preferred.

Please refer to FIG. 2, FIG. 3 and FIG. 4. In the embodiment, the cutting connection segments 220 are of a flat shape. By adopting the above scheme, on the one hand, the contact area of the cutting connection segments 220 and the outer surface of the connection tube 100 and the inner surface of the collapsible tube 300 can be increased, so that the connection strength of the cutting component 200, the connection tube 100 and collapsible tube 300 can be further enhanced to further reduce the risk of cutting component 200 falling off; on the other hand, it can also compress the total outer diameter of the connection tube 100, the cutting connection segments 220 and the collapsible tube 300, that is, to reduce the outer diameter of cutting device. Therefore, the overall outline size of the cutting balloon using the cutting device can be reduced, so as to improve its performance through the blood vessel, that is, to improve the traversing performance of the cutting balloon.

Please refer to FIG. 2, FIG. 3 and FIG. 4. In the embodiment, the cutting component 200 further includes transition connection segments 230 connected between the cutter body 210 and the cutting connection segments 220. The cross-sectional dimension of the transition connection segments 230 are gradually tapered from a side connected to the cutter body 210 to another side. By adopting the above scheme, the transition connection segments 230 are transitionally connected between the cutter body 210 and the cutting connection segments 220, such that the cross-section shape of the cutting component 200 can be gradually changed to the flat shape of the cutting connection segment 220 side, therefore, the connection strength and structural strength between the cutter body 210 and the cutting connection segments 220 can be guaranteed, and the risk of breakage between the cutter body 210 and the cutting connection segments 220 can be avoided, the structural strength of the cutting component 200 can be guaranteed, the service life of cutting component 200 is lengthened, thereby further improving the performance of cutting device.

Please refer to FIG. 2, FIG. 3 and FIG. 4. In the embodiment, the cutting connection segments 220 are formed by an extrusion process or a cutting process. It should be noted here that the cutting connection segments 220 can be flattened by extrusion molding or flattened by cutting molding. Based on the setting of this embodiment, the cutting connection segments 220 can be easily and reliably flattened without damaging the performance of the cutting connection segments 220, the processing convenience is high, and the morphological stability of the cutting connection segments 220 can be effectively maintained.

Please refer to FIG. 5 and FIG. 6. In this embodiment, the cutting connection segment 220 is provided with at least one non-slip ridge 221 on the side surface facing the collapsible tube 300. By adopting the above scheme, on one hand, the contact area of the cutting connection segments 220 and the collapsible tube 300 can be increased, so that the elastic resistance effect of the collapsible tube 300 against the cutting component 200 can be further enhanced, thereby further enhancing the connection strength between the collapsible tube 300, the cutting component 200 and the connection tube 100 to further reduce the risk of the cutting component 200 falling off; on the other hand, it can enhance the friction between cutting connection segments 220 and collapsible tube 300, which further enhancing the connection strength between the cutting component 200 and the connection tube 100 to further reduce the risk of the cutting component 200 falling off.

Please refer to FIGS. 1 and 2. In the embodiment, the collapsible tube 300 is a collapsible tube 300 made of a rubber. By adopting the above scheme, the collapsible tube 300 can have high elasticity of reversible deformation, which can further enhance the elastic resistance of the collapsible tube 300 to the cutting component 200, which further enhancing the connection strength between the cutting component 200 and the connection tube 100 to further reduce the risk of the cutting component 200 falling off.

Please refer to FIG. 2, FIG. 3 and FIG. 4. In the embodiment, the length of the connection tube 100 is greater than 0.5 mm. By adopting the above scheme, the length that the connection tube 100 can be used to connect with the cutting connection segment 220 can be effectively guaranteed, so that the connection strength between the connection tube 100 and the cutting connection segments 220 can be guaranteed to further reduce the risk of the cutting component 200 falling off.

Please refer to FIG. 2, FIG. 3 and FIG. 4. In this embodiment, the length of the connection tube 100 is 1.0 mm. By adopting the above scheme, the length of the connection tube 100 that can be used to connect with the cutting connection segment 220 can be guaranteed, that is, the connection strength between the connection tube 100 and the cutting connection segments 220 can be guaranteed, and the cutting device can pass through tortuous blood vessels, thereby, the ability to pass through tortuous vessels due to the length of connection tube 100 being too long can be avoided.

Please refer to FIGS. 2, 3 and 4. In this embodiment, the ratio of the length of the cutting connection segment 220 to the length of the connection tube 100 is greater than or equal to 0.8. By adopting the above scheme, the connection area of the cutting connection segment 220 and the connection tube 100 will account for more than 80% of the length of the connection tube 100, so that the connection strength between the connection tube 100 and the cutting connection segments 220 can be effectively guaranteed to further reduce the risk of the cutting component 200 falling off.

Please refer to FIG. 2, FIG. 3 and FIG. 4. In this embodiment, the length of the cutting connection segment 220 is equal to the length of the connection tube 100. By adopting the above scheme, the connection area of the cutting connection segment 220 and the connection tube 100 accounts for 1:1 of the length of the connection tube 100, so that the connection strength between the connection tube 100 and the cutting connection segment 220 can be guaranteed to the greatest extent to further reduce the risk of the cutting component 200 falling off.

Figure 7:
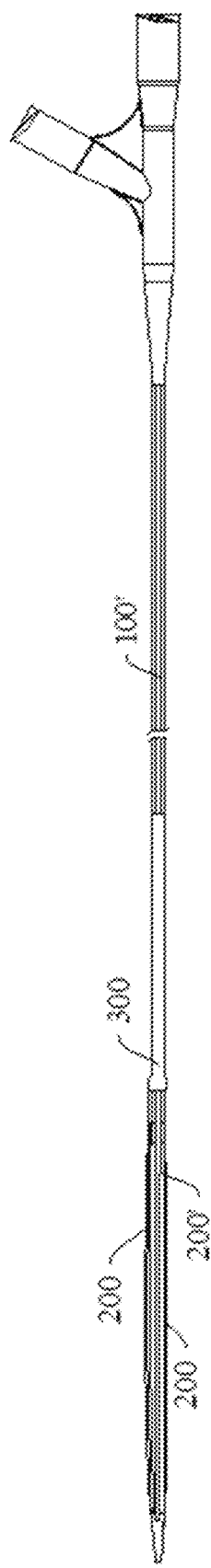
FIG. 7 is a structural schematic view of a cutting balloon provided by an embodiment of the present application.

Please refer to FIGS. 3, 4 and 7. In this embodiment, the cross-sectional shape of the cutter body 210 is arranged in a triangle, a circle or a trapezoid. By adopting the above scheme, the cutter body 210 can have a certain shear stress to ensure and improve the performance of the cutter body 210, that is, the cutter body 210 can be tightly wrapped in the balloon when the balloon body 200' does not reach the lesion location, and the tortuous blood vessel will not be damaged, the cutter body 210 extends and incises the calcified plaque and blood vessel wall along the longitudinal direction of the blood vessel when the balloon body 200' reaches the lesion and expands.

Please refer to FIG. 1, FIG. 5 and FIG. 7, in this embodiment, there are two connection tubes 100 and two collapsible tubes 300, wherein the two connection tubes 100 are respectively connected to two ends of the cutting component 200, and the two collapsible tubes 300 are respectively elastically sleeved on the two connection tubes 100. By adopting the above scheme, two ends of the cutting component 200 use the collapsible tube 300 and the connection tube 100 to achieve the connection of cutting component 200, and to ensure the connection strength between the collapsible tube 300, the cutting component 200 and the connection tube 100, which can further reduce the risk of the cutting component 200 falling off.

Please refer to FIGS. 1 and 3. In this embodiment, there are 3 to 5 cutting components 200. By adopting the above scheme, the processing ability of each cutting component 200 to incise the calcified plaque and the blood vessel wall along the longitudinal direction of the blood vessel can be reliably and effectively guaranteed, that is, the cutting ability of the cutting device is improved. Preferably, three cutting components 200 are provided.

Please refer to FIGS. 1, 3 and 4. In this embodiment, the cutting components 200 are arranged in array relative to a periphery of the connection tube 100. By adopting the above scheme, the cutting components 200 arranged in array relative to the periphery of the connection tube 100 can be spaced, uniformly and effectively cut the vascular calcified plaque on the inner surface of the tortuous blood vessel, that is, the processing ability of each cutting member 200 to incise the calcified plaque and the blood vessel wall along the longitudinal direction of the blood vessel is further improved.

Please refer to FIGS. 2, 3 and 4. In this embodiment, the connection tube 100 is a connection tube 100 made of a metal or alloy that does not transmit X-rays. By adopting the above scheme, on one hand, the connection tube 100 can have a certain structural strength to ensure the connection strength between the connection tube 100 and the cutting component 200, so as to further reduce the risk of the cutting component 200 falling off; on the other hand, it can be based on the performance of the connection tube 100 does not transmit X-rays, such that the connection tube 100 can be clearly developed under X-ray illumination, thereby enabling accurate positioning of the connection tube 100 during surgery, that is, beneficial for accurate positioning of the cutting device during surgery.

Please refer to FIGS. 1, 3 and 4. In this embodiment, the cutting component 200 is a cutting component 200 made of a metal or alloy. By adopting the above scheme, the structural strength of the cutting component 200 can be guaranteed, so that the cutting effect of the cutting component 200 can be guaranteed and improved.

Please refer to FIGS. 1, 3 and 4. In this embodiment, the cutting component 200 is adhered or welded to the peripheral side of the connection tube 100. By adopting the above scheme, the cutting component 200 can be connected to the peripheral side of the connection tube 100 by means of adhering, and can also be connected to the peripheral side of the connection tube 100 by welding, both of which can guarantee and improve the connection strength and convenience of the connection tube 200 and the connection tube 100, and beneficial to further reduce the risk of the cutting component 200 falling off.

Please refer to FIG. 1, FIG. 3, and FIG. 4. In this embodiment, the calculation formula of the length of the cutting component 200 is:

$$y = kx^b$$

Among them, y represents the length of the cutting component 200; x represents the length of the connection tube 100; the value range of k is 55~65; the value range of b is 1.6~1.8. By adopting the above scheme, the length of the cutting component 200 and the length of the connection tube 100 can be in an appropriate power function relationship, so as to prevent the cutting component 200 from being too long and/or the connection tube 100 from being too short and resulting in the connection strength between the cutting component 200 and the connection tube 100 is insufficient, which may cause the cutting component 200 to fall off. That is, based on this embodiment, the length of the cutting component 200 and the length of the connection tube 100 can be designed on the basis of maximizing the cutting effect of the cutting component 200, so as to ensure the connection strength between the cutting component 200 and the connection tube 100, it is beneficial to further reduce the risk of cutting component 200 falling off.

Please refer to FIG. 1, FIG. 3, and FIG. 4, in this embodiment, k=60, and/or, b=1.7. By adopting the above scheme, the length y of the cutting component 200 is equal to 60 times of the length $x^{1.7}$ of the connection tube 100, based on this, the cutting effect of the cutting component 200 and the connection strength between the cutting component 200 and the connection tube 100 can be further balanced, which can further improve the performance of the cutting device.

Referring to FIG. 7, an embodiment of the present application further provides a cutting balloon. The cutting balloon includes a catheter 100', a balloon body 200' connected to the catheter 100' and the cutting device described above. The cutting device is connected to the catheter 100' via the collapsible tube 300. It should be noted here that the collapsible tube 300 is sleeved on the catheter 100' and elastically in contact with the catheter 100', so that the cutting device and the catheter 100' initially establish a stable connection relationship, and then, the collapsible tube 300 and the connection part of the catheter 100 are welded or adhered to further stabilize and secure the connection relationship between the cutting device and the catheter 100'. The balloon body 200' is connected to the catheter 100', and the cutting component 200 is located on the outer surface of the balloon body 200' and closely adheres to the outer surface of the balloon body 200'. When the balloon body 200' is expanded at the lesion, the cutting component 200 of the cutting device can incise the vascular calcified plaque and the blood vessel wall along the longitudinal direction of the blood vessel, which can greatly reduce the loop pressure generated on the blood vessel wall when the balloon body 200' is expanded, the blood vessel damage is reduced. The cutting balloon using the cutting device provided in the above embodiment will have a high connection strength, which can effectively prevent the cutting component 200 from falling off during the operation.

The aforementioned embodiments are only preferred embodiments of the present application, and should not be regarded as being limitation to the present application. Any modification, equivalent replacement, improvement, and so on, which are made within the spirit and the principle of the present application, should be included in the protection scope of the present application.

The invention claimed is:

1. A cutting device, comprising:
   a connection tube;
   a collapsible tube, made of an elastic material and configured to sleeve on the connection tube;
   at least one cutting component, comprising a cutter body and cutting connection segments connected to the cutter body, wherein the cutting connection segments are connected to a peripheral side of the connection tube and are located on the collapsible tube;
   wherein the collapsible tube is in elastic contact against the cutting connection segments; and
   wherein a length y of the at least one cutting component is positively correlated with a b-th power of a length x of the connection tube; and a value range of b is 1.6~1.8.

2. The cutting device of claim 1, wherein the cutting connection segments are of a flat shape.

3. The cutting device of claim 2, wherein the at least one cutting component further comprises a transition connection segment configured to connect between the cutter body and each of the cutting connection segments, and a cross-sectional dimension of the transition connection segment is gradually tapered from a side connected to the cutter body to another side.

4. The cutting device of claim 2, wherein the cutting connection segments are formed by an extrusion process or a cutting process.

5. The cutting device of claim 1, wherein a side surface of each of the cutting connection segments facing the collapsible tube is provided with at least one non-slip ridge.

6. The cutting device of claim 1, wherein the collapsible tube is a collapsible tube made of a rubber.

7. The cutting device of claim 1, wherein the length x of the connection tube is larger than 0.5 mm.

8. The cutting device of claim 7, wherein the length x of the connection tube is 1 mm.

9. The cutting device of claim 1, wherein a ratio of a length of each of the cutting connection segments to the length x of the connection tube is larger than or equal to 0.8.

10. The cutting device of claim 9, wherein the length of each of the cutting connection segments is equal to the length x of the connection tube.

11. The cutting device of claim 1, wherein the cutter body has a triangular, circular or trapezoidal cross-sectional shape.

12. The cutting device of claim 1, wherein two connection tubes and two collapsible tubes are provided, and the two connection tubes are respectively connected to two ends of the at least one cutting component, and the two collapsible tubes are elastically sleeved on the two connection tubes respectively.

13. The cutting device of claim 1, wherein a number of the at least one cutting component is 3 to 5.

14. The cutting device of claim 13, wherein each of the cutting components is arranged in array relative to a periphery of the connection tube.

15. The cutting device of claim 1, wherein the connection tube is made of a metal or alloy that does not transmit X-rays.

16. The cutting device of claim 1, wherein the at least one cutting component is made of a metal or alloy.

17. The cutting device of claim 1, wherein the at least one cutting component is adhered or welded to the peripheral side of the connection tube.

18. A cutting balloon, comprising:
   a catheter; and
   a balloon body, connected to the catheter;
   wherein the cutting balloon further comprises a cutting device connected with the catheter through a collapsible tube, and the cutting device comprises:
   a connection tube;
   the collapsible tube, made of an elastic material and configured to sleeve on the connection tube;
   at least one cutting component, comprising a cutter body and cutting connection segments connected to the cutter body, wherein the cutting connection segments are connected to a peripheral side of the connection tube and are located on the collapsible tube;
   wherein the collapsible tube is in elastic contact against the cutting connection segments; and
   wherein a length y of the at least one cutting component is positively correlated with a b-th power of a length x of the connection tube; and a value range of b is 1.6~1.8.

* * * * *